United States Patent [19]

Yanagisawa et al.

[11] 4,375,762
[45] Mar. 8, 1983

[54] IMPACT-FATIGUE TEST MACHINE FOR GRINDING BALLS

[75] Inventors: Osamu Yanagisawa; Tsuneo Ishigai, both of Hiroshima; Masayoshi Kiyama, Tokyo, all of Japan

[73] Assignee: Nippon Nenryo Company Ltd., Tokyo, Japan

[21] Appl. No.: 257,057

[22] Filed: Apr. 24, 1981

[30] Foreign Application Priority Data

Oct. 15, 1980 [JP] Japan .................. 55-143018

[51] Int. Cl.³ ............................................. G01N 3/30
[52] U.S. Cl. ........................................ 73/12; 73/799; 73/810
[58] Field of Search .................... 73/12, 810, 799, 808

[56] References Cited

U.S. PATENT DOCUMENTS 2,579,503  12/1951  Lubin et al. .................... 73/12

FOREIGN PATENT DOCUMENTS 486533  6/1938  United Kingdom .................. 73/12

Primary Examiner—Jerry W. Myracle

[57] ABSTRACT

A closed system, impact-fatigue test machine for grinding balls comprised of a vertically extending guide member and a lift conveyor wherein the guide member lies above a recessed anvil and defines in its center a longitudinal opening. Each grinding ball is carried upwardly by the conveyor to an opening in the upper portion of the guide member and then is dropped into the guide member to land laterally supported, upon an earlier dropped grinding ball which rests on the anvil below. The earlier dropped ball is then pushed from the anvil toward the conveyor causing the dropped ball to impact the anvil below. The number of dropping cycles that each ball can tolerate without fracture is counted by a counter. Fracture of the balls is detected by a fracture detector.

15 Claims, 12 Drawing Figures

IMPACT-FATIGUE TEST MACHINE FOR GRINDING BALLS

BACKGROUND OF THE INVENTION

1. Field of the Invention

The present invention relates to an impact-fatigue test machine for steel or cast iron balls which are used as grinding balls.

2. Description of the Prior Art

As a result of an increased scale of ball mills and improved ball mill liners, grinding balls are subjected to greater impact forces. Impact resistance of grinding balls is represented mainly by fracture toughness. The conventional impact tests used to determine impact resistance are Izod tests, Charpy tests, and tensile strength tests. These tests, however, fail to be an adequate means of testing impact resistance due to the difficulties in preparing test pieces from the hard materials of which grinding balls are made and due to the tests' inabilities to simulate the actual impact forces experienced in ball mills. In the case of cast-iron grinding balls, it was impossible to obtain accurate measured values of impact resistance by means of the above mentioned tests. The tests fail to evaluate the difference in actual fracture toughness of a ball based on a slight difference in the material of the balls.

In a ball mill that portion of a ball which impacts another ball is subjected to complex, three-dimensional stresses. The above-mentioned tests fail to provide results that correlate well with the actual fracture toughness or the impact fatigue life of grinding balls in a ball mill.

Recently, various types of impact fatigue test machines have been proposed or developed in an attempt to evaluate the fracture toughness of grinding balls under repeated conditions. For example, a test machine of this kind is disclosed in the *Journal of the Iron and Steel Institute*, 197, (1961), PP. 40–48 (R.H.T. Dixon). This machine is depicted in FIG. 1 and includes an anvil 101 made of Ni-Hard cast iron, with an upper surface inclined at a 30 degree angle. Each grinding ball to be tested is individually carried by means of a lift conveyor 102 up to an upper chute 103, which introduces the ball into the upper end of a drop-guide member 104.

The ball drops from the upper end of the drop guide member 104 vertically downwards and impacts upon the anvil 101 lying below. Upon such impact, the ball rebounds several times against a rebound plate 104. After the rebounding motion has stopped, the ball rolls along a lower chute to the lower portion of the lift conveyor to repeat the cycle. This system then, subjects a ball to repeated impact cycles. The cycle is stopped when the ball fractures. *Foundry Trade Journal*, 1973, 5, P. 645, describes the test results obtained by the machine shown in FIG. 1 which was used to test balls made of nodular cast iron, high chrome steel based on, austenite, high chrome steel based on martensite etc. The journal concludes that the effect of anvil 101 on the test results cannot be excluded.

In *Symposium, Materials for the Mining Industry*, 1974, PP. 189–195, the test results obtained by the above-mentioned machine for balls of white cast iron and other materials are discussed. The results of these tests failed to correlate well with the actual life and toughness of balls used in ball mills.

SUMMARY OF THE INVENTION

The principal object of the present invention is to provide an improved impact-fatigue test machine whose test results have a high correlation to the actual life and durability of ball used in ball mills.

Another object of the present invention is to provide a test machine which is capable of automatically detecting ball fractures.

A further object of the present invention is to provide a test machine which is adjustable to impart varying impact forces.

A still further object of the present invention is to provide a test machine capable of accommodating varying sized balls by means of adjustment of the cross-sectional area of the vertically extending guide passage.

These and other features and advantages of the present invention will become apparent from the following description in connection with the accompanying drawings.

DETAILED DESCRIPTION OF THE PREFERRED EMBODIMENTS

Figure 1:
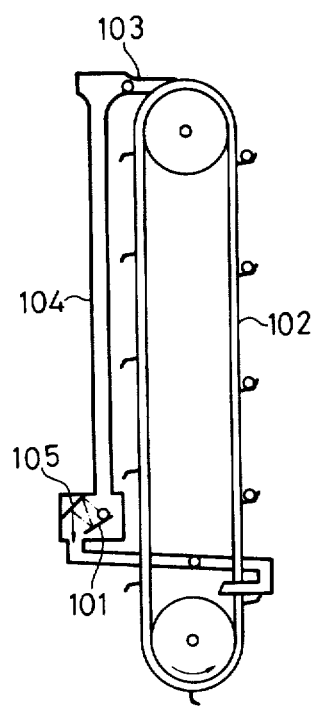
FIG. 1 is a schematic view showing the above-mentioned conventional test machine.

Referring now to FIGS. 2 to 7, there is shown a first embodiment of the present invention which comprises a vertically extending, elongated guide member 1, an anvil 2 below the lower end 3 of the guide member 1, a pusher 4 for horizontal reciprocal movement pusher 4 being disposed between the lower end 3 and the anvil 2, and a bucket conveyor 5 extending along guide member 1. The ball 6 and the other balls to be tested are individually lifted by the conveyer 5, to the upper portion 7 of the guide member 1, and then dropped into guide member 1. First ball 6A rests on the anvil 2. Ball 6 is then dropped down guide member 1 to impact against ball 6A. Accordingly, balls 6 and 6A are subjected to impact forces in substantially the same manner as in the actual ball mills. On the upper surface of the anvil 2, there is formed a recess 8 which is shaped to hold ball 6A. The recess is formed in a substantially conical configuration and opens upwardly toward the lower end 3 of the guide member 1 to receive each ball successively. After ball 6 is impacted by ball 6 it is laterally pushed out of the recess 8 by means of the pusher 4 which, in this case, consists of an air-cylinder. The pusher 4 is positioned on that side of the anvil 2 which is remote from the conveyer 5 so that the ball 6A is pushed out of the recess 8 and rolled toward the conveyer 5.

Figure 3:
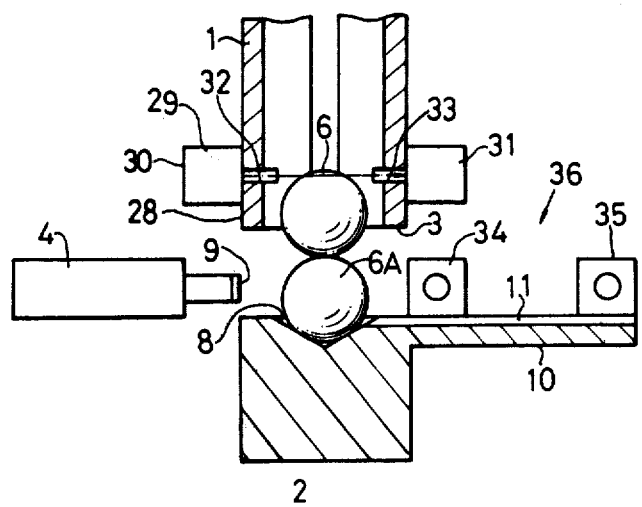
FIG. 3 is an enlarged longitudinal sectional view of the lower portion of the test machine shown in FIG. 2 including one embodiment of a fracture detecting means.

As shown in FIG. 3, the pusher 4 has a piston rod including a rubber plate 9 at the outer end thereof. The plate 9 serves to absorb the impact force which would otherwise be applied to that part of the ball 6A which is brought into direct contact with the piston rod. The anvil 2 is provided with a lower chute 10 extending horizontally toward the conveyer 5.

Figure 4:
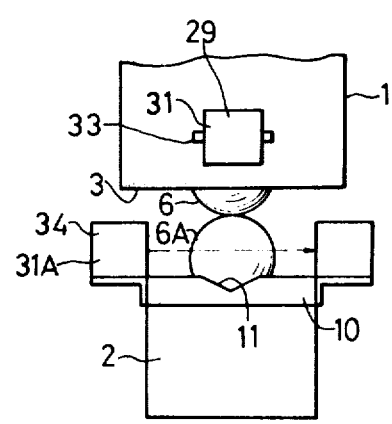
FIG. 4 is a right side view of FIG. 3.

The chute 10 includes an upper surface guide path 11 extending from the recess 8 to the end of the chute 10, adjacent conveyor 5. The path 11 guides the balls pushed out of the recess 8 to the conveyer 5 (FIGS. 3 and 4).

The conveyer 5 comprises upper and lower pulleys 12 and 13, endless belt 14, and a plurality of buckets 15 which are pivotally connected to the outer surface of the belt 14.

Figure 2:
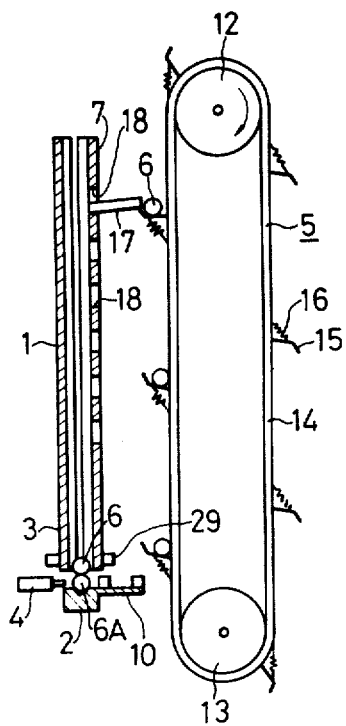
FIG. 2 is an elevational view, partly in section, of the test machine according to one embodiment of the present invention.
Figure 5:
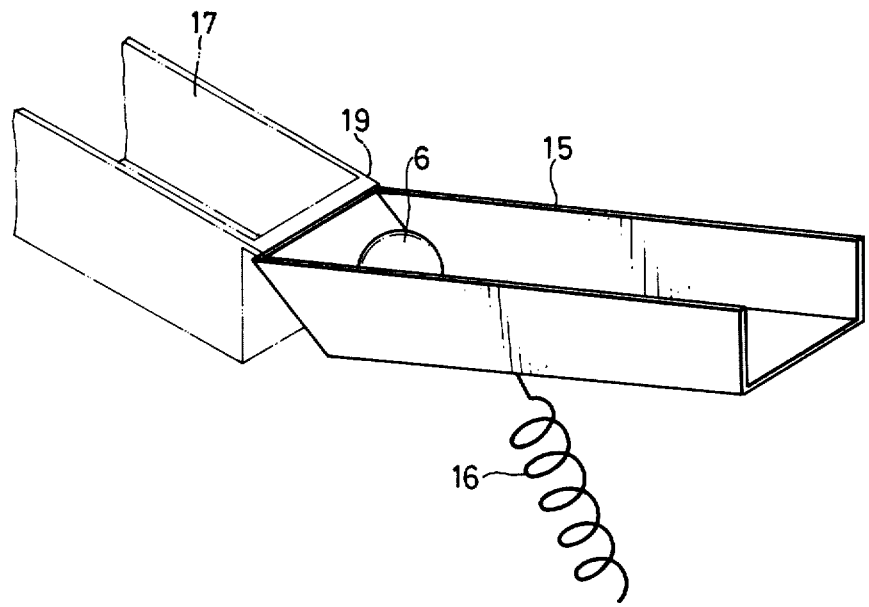
FIG. 5 is a perspective view of the upper portion of the test machine shown in FIG. 2.

Each bucket 15 is biased in the direction of movement of the belt 14, by means of a compression coil spring 16 (FIGS. 2 and 5). The guide member 1 is provided with an upper chute 17 for supplying balls 6 from the buckets 15 of the conveyor 5 to the upper portion 7. In order to adjust the dropping height of the ball within a range preferably between 2 and 5 m, the chute 17 is detachably inserted into a selected one of apertures 18 formed at predetermined longitudinal distances along the guide member. As shown in FIG. 5, an engaging lip 19 projects from the outer end of the chute 17 toward the conveyer. The lip 19 engages with and pushes down the outer end of the bucket 15, so that the ball 6 rides over the end of the bucket 15 and the lip 19, and rolls into the chute 17.

Figure 6:
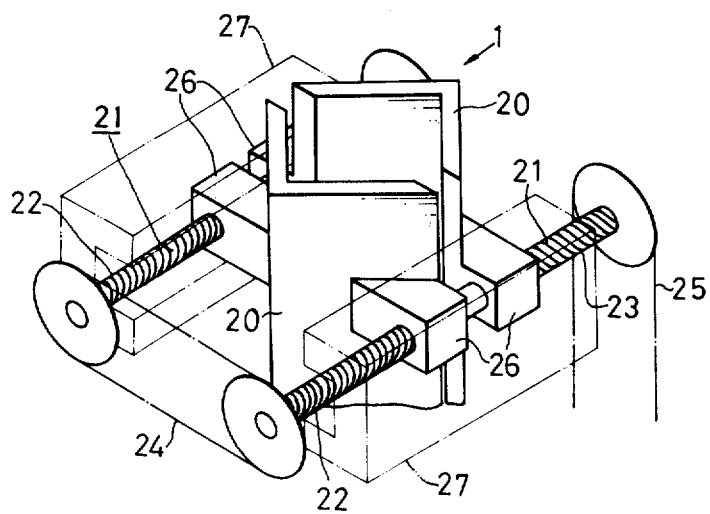
FIG. 6 is a perspective view of an adjusting mechanism for the guide member of the test machine shown in FIG. 2.

As shown in FIG. 6, the guide member 1 includes a tube having a substantially rectangular cross-section. This tube is divided diagonally by a pair of channel members 20, 20. The channel members 20 are coupled to each other by a plurality of horizontally extending threaded shafts 21, each of which engage with said channel members 20 by means of threads 22, 23. Consequently, the channel members 20, 20 may be symmetrically and diagonally moved toward or away from each other thereby maintaining the center axis of the tube in its original position while adjusting the cross-sectional area of the guide to accommodate balls of varying diameters (conventionally between 50 and 100 mm). This means of adjustment successfully serves to guide all tested balls toward the center of the recess 8.

The upper and lower portions of the guide 1 are both adjustable by means of the pair of above-mentioned threaded shafts 21, 21 (in FIG. 6, the lower pair of the shafts is not illustrated). Each pair of shafts 21, 21 are connected to each other by an endless chain 24. The upper pair of shafts and the pair of lower shafts are connected by means of an endless chain 25. One of the lower shafts is driven by a suitable driving means (not shown), for example and electric, pneumatic or hydraulic motor. By such an arrangement, the shaft 21 driven by the driving means drives three other shafts to provide a synchronous motion. Channel members 20 are integrally attached to horizontally extending ribs 26. The ribs 26 are slidably engaged with guide channels 27 and are thereby guided during the diagonal adjustment of channel members 20. As shown in FIGS. 3 and 4, the lower end 3 of the guide member 1 is shaped similarly to supporting means 28. Supporting means 28 supports the periphery of the ball 6 as it rests on the ball 6A. Due to the impact force, the ball 6 rebounds several times against the ball 6A. After the rebound motion is completed, the ball 6 is supported at its periphery by the supporting means 28 resting on the ball 6A. There is mounted on the lower end 3 of the guide member 1 a fracture device 29 comprising a light source 30 and a photoelectric cell 31. The light source 30 emits a light beam through a slit 32 toward the top of the ball 6 resting on the ball 6A. When the ball 6 is free from fracture at the top or the bottom thereof and therefore its diameter is unchanged, the top of the ball 6 is at a sufficient height to interrupt the light beam. Due to this interruption, the light beam cannot reach the cell 31. On the other hand, when the ball 6 has fracture and the top thereof does not interrupt the light beam, the cell 31 receives the light beam through a slit 33 and thus detects the fracture of the ball. On the chute 10, there are mounted a pair of detectors 34, 35 which jointly form a fracture detector 36. The detectors 34, 35 are positioned along the guide path 11 and are spaced a predetermined distance from each other along longitudinally guide path 11. A ball without fracture rolls faster than a ball with a fracture. Detectors 34 and 35 have therefore been positioned to detect the speed at which a ball 6 rolls along guide path 11. The detector 36 detects a fracture in a ball 6 by measuring the time length in which the ball rolls from one detector 34 to the other detector 35.

Figure 7:
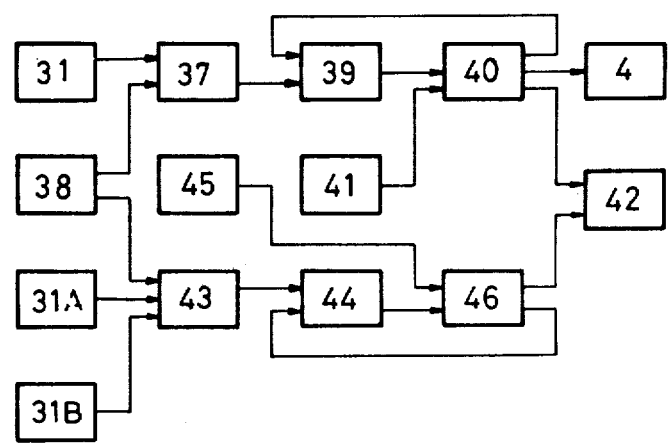
FIG. 7 is a block diagram of the control system for the test machine shown in FIG. 2.

FIG. 7 shows one embodiment of the control system which can suitably be used in the above described test machine. The detector 31 is connected to a gate circuit 37 to which clock pulses are supplied from a pulse generating circuit 38. The light beam is intermittently interrupted when the ball 6 rebounds. The gate circuit 37 allows the clock pulses to be supplied to a counter 39 during the period in which the cell 31 receives the beam. The counter 39 feeds a signal representing the integrated number of the clock pulses to a comparator 40, into which a set value signal is also supplied from a setting adjuster 41. The signal representing the integrated number is compared with the set value signal. When the integrated number reaches the set value, the comparator 40 feeds a control signal to the electric source 42 to cut it off. When the counting of the clock pulses is interrupted before the integrated number reaches the set value, the comparator 40 feeds control signals to the pusher 4 and to the counter 39. One of the signals operates the pusher to make it push the ball 6A resting on the recess, and the other signal resets the integrated number to zero. The photoelectric receptors 31A, 31B of detectors 34, 35 are connected to a gate circuit 43, to which said clock pulses are also supplied. The gate circuit 43 allows the pulses to pass through when the rolling ball interrupts the light beam directed toward detector 34 unless ball 6 subsequently interrupts the light beam received by the detector 35. The pulses passing through the gate circuit 43 are fed to a counter 44. The integrated number of pulses at the output of the counter 44 is compared with the set values of an adjuster 45 by means of a comparator 46. When the number exceeds the predetermined value, the comparator 46 cuts off the power source 42. On the other hand, when the integrated number is smaller than the set value, the controller 46 only resets the counter 44 to zero.

Figure 8:
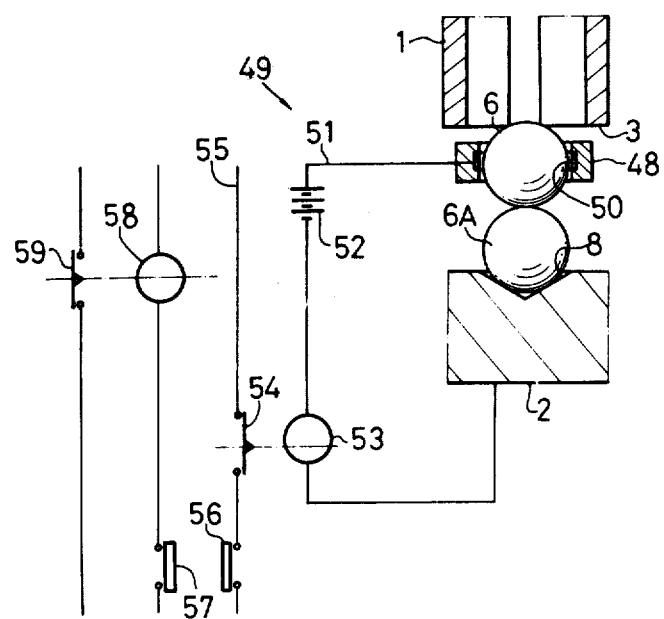
FIG. 8 shows another embodiment of the fracture detecting means.

FIG. 8 shows a second embodiment of the present invention in which the supporting means 48 which acts to laterally support the ball 6 on the resting ball 6A, is separated from the guide member 1. The supporting means 48 consists of a ring of electrical insulating material. A fracture detecting device 49 includes an annular electrode 50 mounted on the inner surface of the ring 48 and connected to circuit 51. Circuit 41 is comprised of electrode 50 electrically connected to a DC voltage source 52 and relay coil 53 of which connects to the anvil 2. When the ball 6 is free from fracture and therefore has maintained its original diameter measurement, it contacts electrode 50. In this position ball 6 is also in contact with the ball 6A and therefore the anvil 2, so that relay coil 53 is energized to cause a normally-open on-delay contact 45 to close. However, when the ball 6 is fractured and thus causes an interruption of the contact to electrode 50, the coil 53 is not energized. Thus, circuit 51 operates only when the ball 6 or 6A is free from fracture. The contact 54 closes circuit 55 for operating the pusher 4. The pusher 4 has a limit switch 56 at the forward end of the piston rod which opens the circuit 55 when the rod pushes the ball 6A out of the anvil 2. At that time, the piston rod is returned back to its initial position by means of a spring (not shown). At the initial position, the pusher 4 closes another limit switch 57 to energize a coil 58 of a relay. The relay coil 58 makes a normally closed type on-delay contact 59 open when, during a predetermined period, the pusher 4 is not being operated, (when ball 6 does not come into continuous contact with the electrode 50 because of fracture). The contact 59 is included in the circuit of the power source 42 which is connected to the pusher 4 and the conveyor 5. Thus when the detecting device 49 detects that a ball 6 is fractured, the machine is stopped. The pusher 4 is provided with a counter (not shown) which records the number of times a ball 6 is pushed onto the conveyor 5 thereby automatically recording the durability of the ball 6 being tested.

Figure 9:
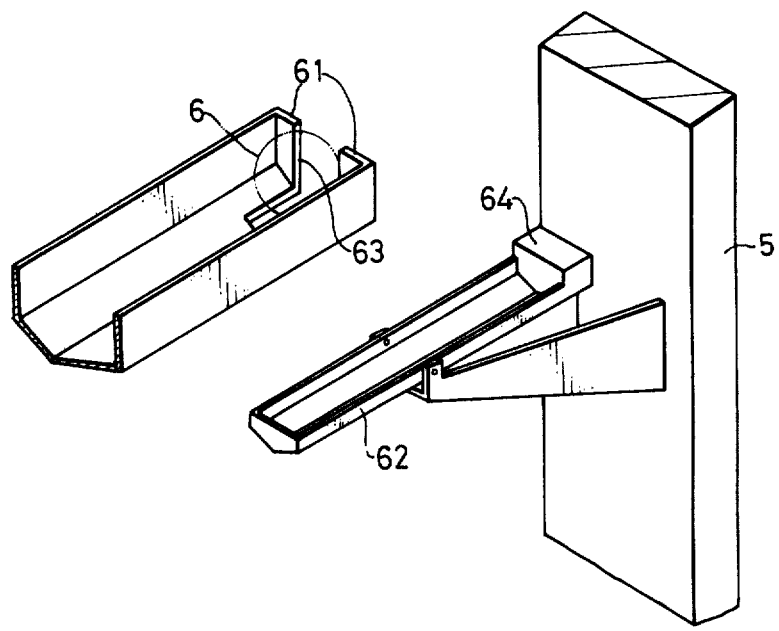
FIG. 9 shows the lower portion of a test machine according to another embodiment of the present invention.
Figure 10:
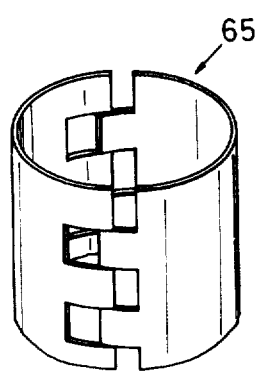
FIG. 10 shows another type of guide member used in the test machine of the present invention.
Figure 11:
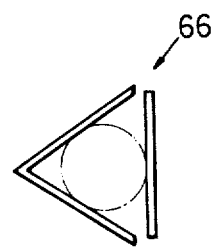
FIG. 11 shows still another type of guide member.

FIG. 9 shows another embodiment of the lower chute 60. The chute 60 has a stopper 61 used to hold the ball 6 when the conveyor bucket is not in a position to receive it. The bucket 62 passes upwards through a notch 63 formed in the outer end of the chute 60 to receive the ball 6. The outer end of the bucket 62 adjacent to the chute 60 is biased upwardly by a counterweight 64 at the inner end thereof. By this arrangement, there is no need to synchronize the movements of pusher and the conveyer as the chute 60 holds the ball until it can be received by the bucket 15. FIG. 10 and FIG. 11 show a further embodiment of guide members 65,66. In both figures the guide members are comprised of two relatively movable parts which are adjustable to accommodate balls of varying diameters.

The test results obtained by the test machine according to the present invention will now be explained. There are two types of fractures to which grinding balls are susceptible in ball mills. The first is the flaking type fracture, in which thickness of several millimeters at the surface of the ball flakes away. The second is the separating type fracture in which separation occurs substantially along a plane which passes through the center of the ball. The test machine of the present invention is capable of causing both types of fractures and is therefore an effective tool for evaluating the durability of a grinding ball during actual use.

The test results of the present invention are measured by recording the number of times a ball can withstand being dropped (Ns) before flaking is detected, and the number of times the ball may be dropped (Nf) before a fracture affecting its ability a roll is detected. We may define a flaking rate $-dW/dN$ as follows:

$$-dW/dN = \Delta Wf/Nf$$

where dW is the difference between the weight of a ball without flaking and the weight of a ball with flaking and $\Delta Wf$ is total weight loss divided by the number of drops Nf.

Figure 12:
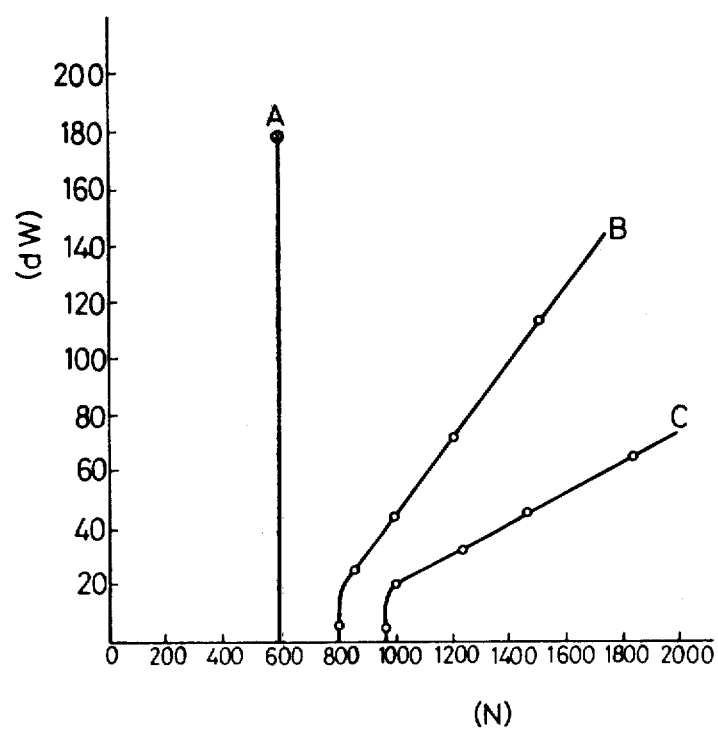
FIG. 12 is a graph which shows the test results obtained by the test machine according to the present invention.

FIG. 12 is a graph of results arrived at in testing several types of balls available on the market. The diameter of the balls was 90 mm$\phi$. The dropping height was 5 m. Curve A is a dW-Nf curve for a low chrome, white cast-iron ball. From curve A it can be seen that the ball did not exhibit a decrease in weight (dW) due to flaking until Nf reached about 600. As the Nf reached about 600, the ball began to flake and continued to flake more severely as the test continued. Curves B, C are illustrative of the dW-Nf characteristics of high chrome, cast-iron balls, which were heat-treated under varying conditions. The ball of curve C exhibited flaking when Nf reached about 800. Flaking then increased as the tests continued ($dW/dN = 14.4 \times 10^{-4}$ [g/N]). The ball of curve B began to exhibit flaking at about 1000 Nf, but did not flake as severly during continued testing as did the ball illustrated by curve C, (i.e., $dW/dN = 5.39 \times 10^{-2}$ [g/N]). In later use of balls of the type tested in curves A, B and C in a grinding mill, their actual durability correlated very well with the above-mentioned test results. Further test results obtained by the machine according to the present invention are shown in the following table.

| curve | balls tested (90mm $\phi$) | Nf | broken state |
|---|---|---|---|
| A | low chrome, cast-iron surface hardness HR 48–50 | 610 | slightly broken in flaking manner. The test could be continued |
| B | high chrome, cast iron surface hardness HR 60–61 | 1490 | largely broken in flaking manner |
| C | high chrome cast iron surface hardness HR 62–64 | 1840 | largely broken in flaking manner or broken in separating manner |

In the above table, Nf denotes the number of times a ball was dropped before it exhibited flaking of a diameter of 60–70 mm$\phi$ and become unrollable. It will be appreciated that the above-noted results were obtained by a machine according to the present invention. These test results exhibit close correlation to the actual usable life of a ball in a grinding mill. The test machine according to the present invention only simulates the actual stress balls are subjected to in a grinding mill and is an accurate predictor of the useful life of such balls. While the present invention has thus far been described with reference to specific embodiments, it is to be understood that the invention is not limited thereby. Various modifications may be made to the present invention without departing from the spirit and scope of the invention as claimed below.

We claim:

1. An impact-fatigue test machine for grinding balls comprising:
   a vertically extending guide means which guides dropping balls and has an upper portion and a lower end;
   an anvil means below the lower end of said guide means, said anvil means having a recess which opens upwardly toward said lower end to receive the ball successively;
   a counter means to count the number of the balls received by the recess of said anvil means;
   a supporting means which supports the periphery of a ball on a preceding ball that rests on the recess of said anvil means;
   pushing means which pushes said preceding ball out of said recess;
   a lifting means which lifts the ball pushed out of said recess up to the upper portion of said guide means; and
   a detecting means to detect fracture of said balls.

2. The machine as claimed in claim 1, further comprising an upper chute which supplies said balls from said lifting means to the upper portion of said guide means.

3. The machine as claimed in claim 2, wherein the height of said upper chute means is vertically adjustable.

4. The machine as claimed in claim 3, wherein said guide means includes a plurality of apertures which open toward the lifting means and are aligned vertically so as to receive said upper chute in a selected one of said apertures.

5. The machine as claimed in claim 1, further comprising a lower chute which supplies the ball pushed out of said recess to said lifting means.

6. The machine as claimed in claim 5, wherein said detecting means is adapted to detect the fracture of the balls by decrease of the rollability of said balls on said lower chute.

7. The machine as claimed in claim 6, wherein said detecting means includes a timer means which measures the length in time in which the ball rolling on the lower chute moves over a predetermined distance so as to evaluate the rollability.

8. The machine as claimed in claim 1, further comprising a control means cooperating with said detecting means to control the operation of said pushing means.

9. The machine as claimed in claim 8, wherein said control means controls also the operation of said lifting means.

10. The machine as claimed in claim 1, wherein said detecting means detects fracture of said balls photoelectrically.

11. The machine as claimed in claim 1 or 10, wherein said detecting means is adapted to detect the fracture of the balls by detecting the decrease of the diameter of said balls.

12. The machine as claimed in claim 11, wherein said detecting means includes a timer means which measures the length in time of period during which the top of the ball on another ball resting on the recess is kept higher than a predetermined level.

13. The machine as claimed in claim 1, wherein said detecting means includes a circuit means which is short-circuited by one of said balls having fracture.

14. The machine as claimed in claim 1, wherein said lifting means lifts said balls in variable lifting speed.

15. The machine as claimed in claim 1, wherein said guide means includes a path to guide the dropping movement of the balls, the cross-sectional dimension of said path being variable corresponding to the diameter of said balls.

* * * * *